United States Patent [19]

Bernard et al.

[11] Patent Number: 5,262,157
[45] Date of Patent: Nov. 16, 1993

[54] METHOD OF PREVENTING *PNEUMOCYSTIS CARINII* PNEUMONIA USING PENTAMIDINE IN AN AEROSOL FORM

[75] Inventors: Edward M. Bernard; Donald Armstrong, both of New York, N.Y.

[73] Assignee: Sloan-Kettering Institute for Cancer Research, New York, N.Y.

[21] Appl. No.: 287,487

[22] Filed: Dec. 20, 1988

Related U.S. Application Data

[63] Continuation of Ser. No. 30,873, Mar. 26, 1987, abandoned.

[51] Int. Cl.$^5$ .................................................. A61L 9/04
[52] U.S. Cl. .................................... 424/45; 424/40; 424/54; 424/86; 514/631; 514/636; 514/885; 514/957; 514/958
[58] Field of Search .............. 424/45, 40, 54, 86; 514/631, 636, 885, 957, 958

[56] References Cited

U.S. PATENT DOCUMENTS 4,119,096  10/1978  Drews .......................... 128/200.16
4,649,911  3/1987  Knight et al. .................. 128/200.21

OTHER PUBLICATIONS

Navin et al., "Intravenous Versus Intramuscular Administration of Pentamidine", [Letter]. N. Engl. J. Med. 1984; 311:1701-2.
Waldman et al., "Pentamidine Isethionate Levels In Lungs, Livers, and Kidneys of Rats After Aerosol or Intramuscular Administration", Amer. Rev. Resp. Dis., 108:1004-6 (1973).

*Primary Examiner*—John Kight, III
*Assistant Examiner*—Sam A. Acquah
*Attorney, Agent, or Firm*—John P. White

[57] ABSTRACT

*Pneumocystis carinii* pneumonia may be prevented in a subject susceptible to infection by *Pneumocystis carinii* by administering to the subject an amount of a pentamidine in aerosol form effective to prevent infection by *Pneumocystis carinii* and thus prevent *Pneumocystis carinii* pneumonia. Also, this invention provides a composition for the prevention of *Pneumocystis carinii* pneumonia which comprises an amount of a pentamidine effective to prevent infection by *Pneumocystis carinii* and thus prevent *Pneumocystis carinii* pneumonia in aerosol form and a pharmaceutically acceptable carrier.

4 Claims, 2 Drawing Sheets

FIGURE 2

METHOD OF PREVENTING *PNEUMOCYSTIS CARINII* PNEUMONIA USING PENTAMIDINE IN AN AEROSOL FORM

This invention was made with government support under Grant Number AI-21938 from the National Institute of Allergy and Infectious Diseases, U.S. Department of Health and Human Services. The U.S. Government has certain rights in this invention.

This is a continuation of application Ser. No. 030,873 filed Mar. 26, 1987, now abandoned.

BACKGROUND OF INVENTION

Throughout this application various publications are referenced by numbers within parentheses. Full citations for these publications may be found at the end of the specification immediately preceding the claims. The disclosures of these publications in their entireties are hereby incorporated by reference into this application in order to more fully describe the state of the art to which this invention pertains.

*Pneumocystis carinii* pneumonia (PCP) is the most common life-threatening opportunistic infection in patients with acquired immunodeficiency syndrome (AIDS). There is no safe and effective prophylaxis for this infection in patients with AIDS. Prevention of PCP would mean a reduction in mortality, morbidity, and medical costs. Treatment of the infection is costly, facilities for its diagnosis and treatment are scarce, and the number of people at risk is increasing.

Pneumonia due to *Pneumocystis carinii* occurs in patients with AIDS and in cancer and organ transplant patients. The infection has also been seen in epidemics among premature and malnourished infants. The report in 1981 of PCP in otherwise healthy male homosexuals signaled the emergence of the AIDS epidemic (1). More than 65% of AIDS patients develop PCP (2). In many cases the development of PCP is the first sign of immune dysfunction and thus provides the basis for the diagnosis of AIDS.

Trimethoprim-sulfamethoxazole (SXT) is effective in the prevention and treatment of PCP in experimental animals and in humans. Prophylaxis with SXT has markedly decreased the incidence of PCP among patients with leukemia or lymphoma. Unfortunately, 60–70% of patients with AIDS have adverse reactions to SXT (3). These patients cannot receive SXT prophylaxis and, if they develop PCP, must receive pentamidine.

Pentamidine was the first effective treatment for PCP. It is highly effective in treatment of PCP infection in patients with AIDS. The drug is presently administered by IV infusion or IM injection at 4 mg/kg/day for 14–21 days. Unfortunately, treatment often causes severe toxic reactions including hypotension, renal failure, and hypoglycemia (4). Response to therapy is slow and patients require prolonged hospitalization and intensive, supportive care.

Pentamidine isethionate is an effective form of pentamidine. Pentamidine isethionate has a molecular weight of 592.68 and has the following structure:

$$\underset{NH_2}{\overset{\overset{NH}{\|}}{C}}-\!\!\!\left\langle\;\;\right\rangle\!\!\!-OCH_2(CH_2)_3CH_2O-\!\!\!\left\langle\;\;\right\rangle\!\!\!-\underset{NH_2}{\overset{\overset{NH}{\|}}{C}} \quad 2\;\begin{array}{l}CH_2OH\\CH_2SO_3H\end{array}$$

Pentamidine is also sold as the naphthoate. Both forms are sold as antiprotozals.

There are currently no methods available for prevention of PCP which have been proven to be safe and effective among patients with AIDS. Several methods are being investigated in clinical trials: these include sulfamethoxazole-trimethoprim (bactrim), sulfadoxinepyrimethamine (fansidar), dapsone, or monthly iv pentamidine. Aerosol pentamidine appears to offer significant advantages over these methods. Because the drug is applied topically there is efficient delivery to the target organ and little systemic absorption. This limits toxicity and provides increased effectiveness.

Pentamidine is effective in the chemoprophylaxis of African trypanosomiasis (sleeping sickness) (7). Human volunteers, subjected weekly to bites from infected tse-tse flies, resisted infection for one year or more after a single IM dose of pentamidine (8). Twice-yearly IV or IM doses eliminated the infection in endemic areas in subsaharn Africa. The drug has been administered to more than ten million people in campaigns to eradicate sleeping sickness. However, no adequate studies of prevention of PCP in humans with IV or IM pentamidine have been reported. In fact, prophylaxis with IV or IM pentamidine was unsuccessful in the animal model of PCP (9).

The route of administration of pentamidine profoundly affects its tissue distribution. After IV or IM administration pentamidine is eliminated rapidly from blood, it accumulates in tissues, and is eliminated slowly from them. The amount of pentamidine that accumulated in the lungs of rats or humans that received IV or IM pentamidine was a small fraction of the amounts that accumulated in other visceral organs. An earlier study showed that aerosol administeration of pentamidine favor its distribution to the lung. However, the relationship between tissue levels and dosage was not determined (10).

The aerosol route delivers pentamidine to the target organ while limiting potentially-toxic accumulation in other organs. The drug is retained in the lungs for many weeks after a single aerosol dose; the half-life of elimination from the lungs in rats was 36 days. Low and infrequent treatment with aerosol pentamidine was highly effective in prevention of PCP in the animal model. No toxicity was seen in histopathologic sections from the lungs of rats that received aerosol pentamidine at doses that greatly exceeded the therapeutic dose (5).

A previous article discloses a new Bioassay for studying pentamidine pharmacokinetics (5). In this article the authors speculate that a better understanding of the pharmacokinetics of pentaimidine should lead to safer, more effective use of the drug in the treatment or prevention of PCP. Elsewhere in the paper, the authors note that aerosol administration also deserves further study. However, there is no disclosure that administration of pentamidine in aerosol form to subjects suseptible to infection by *Pneumocystis carinii*, particularly effective in preventing *Pneumocystic carinii* infection and the PCP caused thereby.

An abstract disclosing the use of pentamidine in an aerosol for prevention of PCP was distributed on Mar. 26, 1986 to attendees at the Annual Meeting of the American Society for Microbiology, Washington, D.C.

SUMMARY OF THE INVENTION

*Pneumocystis carinii* pneumonia may be prevented in a subject susceptible to infection by *Pneumocystis carinii* by administering to the subject an amount of a pentamidine in aerosol form effective to prevent infection by *Pneumocystis carinii* and thus prevent *Pneumocystis carinii* pneumonia.

Also, this invention provides a composition for the prevention of *Pneumocystis carinii* pneumonia which comprises an amount of a pentamidine effective to prevent infection by *Pneumocystis carinii* and thus prevent *Pneumocystis carinii* pneumonia in aerosol form and a pharmaceutically acceptable carrier.

BRIEF DESCRIPTION OF THE FIGURES

FIG. 2. shows a semi-log plot of pentamidine concentrations in the lungs of rats that had received a single dose of 4.0 mg/kg of pentamidine by aerosol.

DETAILED DESCRIPTION OF THE INVENTION

Figure 1:
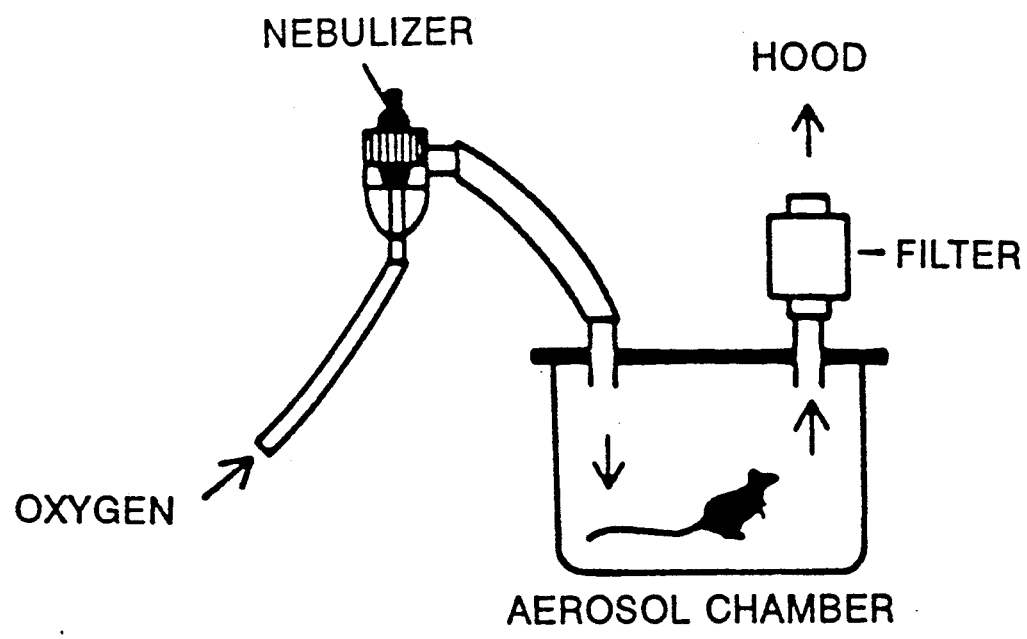
FIG. 1. shows an apparatus used to administer aerosol pentamidine to rats.

*Pneumocystis carinii* pneumonia may be prevented in a subject susceptible to infection by *Pneumocystis carinii* by administering to the subject an amount of a pentamidine in aerosol form effective to prevent infection by *Pneumocystis carinii* and thus prevent *Pneumocystis carinii* pneumonia.

Preferably, the subject is a human being who has been infected by the virus which causes acquired immune deficiency syndrome (AIDS) or one who has cancer or will receive an organ transplant or is otherwise immunosuppressed.

The pentamidine useful in the practice of this invention may be pentamidine isethionate or pentamidine naphthoate, particularly the former. Other salts of pentamidine are known and would be useful in the prevention of PCP.

The pentamidine in aerosol form may be administered by intranasal inhalation as well as by oral inhalation. The intrasasal or oral inhalation may be effected utilizing an ultrasonic nebulizer, metered dose inhaler, or other such device.

For human use the amount of pentamidine in aerosol form effective to prevent infection by *Pneumocystis carinii* may vary widely but is typically between about 0.1 microgram/ml and about 200 micrograin/ml. The amount of pentamidine contained in the aerosol is typically about 0.5 mg to about 500 mg. The prefered amount of pentamidine contained in the aerosol is about 30 mg to about 60 mg. Pentamidine in aerosol form may be effective to prevent infection by *Pneumocystis carinii* upon inital administration. Although the pentamidine may be administered in aerosol form weekly, or every 3 or 4 days, it is presently perferred that pentamidine in aerosol form be administered every 3 or 4 days for about 2 weeks and thereafter administered weekly.

This invention also provides a composition for the prevention of *Pneumocystis carinii* pneumonia. This composition comprises an amount of a pentamidine effective to prevent infection by *Pneumocystis carinii* and thus prevent *Pneumocystis carinii* pneumonia in aerosol form and a pharmaceutically acceptable carrier. The pharmaceutically acceptable carrier may be any of the currently well known such carriers. An example of such carriers is sterile, pyrogen-free water. The amount of the pentamidine effective to prevent infection by *Pneumocystis carinii* may vary widely but typically is between about 0.1 micrograin/ml and about 200 micrograin/ml and the amount of pentamidine contained in the aerosol is typically about 0.5 mg to about 500 mg. The pentamidine may be pentamidine isethionate or pentamidine naphthoate.

The following experimental details are set forth to aid in understanding the invention, but are not intended to, and should not be construed so as to limit in any way the scope of the invention as set forth in the claims which follow.

I. Animal Studies

We compared the tissue distribution of pentamidine in experimental animals treated with IM or aerosol pentamidine. We also tested the toxicity of aerosol pentamidine in rats and tested its effectiveness in an experimental model of *Pneumocystis carinii* pneumonia (PCP).

Measurement of Pentamidine in Tissues

All doses and concentrations of pentamidine were calculated in terms of the di-isethionate salt: 1.74 mg of the salt equals 1.00 mg of the base. Intramuscular (IM) doses were administered to the hindcalves of male Sprague-Dawley rats (240–260 g, Charles River Breeding Laboratories, Wilmington, Mass.). An agar-diffusion bioassay was used as described to measure pentamidine concentrations in tissue (5).

Administration of Aerosol Doses

The method used to treat rats with aerosol pentamidine is illustrated in FIG. 1. The dose was calculated from the product of the concentration of the drug in the chamber, the minute volume of the rats (lung vol.-×resp. rate), and the time of exposure. In all experiments exposure time was 15 min, male Sprague-Dawley rats with an average weight of 250 g were used, and the minute volume of the rats was assumed to be 70 ml. Rats were treated in groups of four. They were placed in the glass chamber while it was swept with a stream of aerosolized pentamidine. The aerosol was generated by oxygen flowing at 8 l/min through the nebulizer (Cadema Medical Products, part no. CA 61, Middletown, N.Y.). The drug solution was aerosolized at 0.3 ml/min with an expected mean particle diameter of 0.5–0.8 micron. To deliver a dose of 4.0 mg/kg the neubulizer was charged with 4.5 ml of a 25 mg/ml solution of pentamidine isethionate in water. During the 15 min exposure time, 120 l of oxygen and 112.5 mg of pentamidine flowed through the chamber. The concentration of pentamidine in the atmosphere of the chamber was thus about 0.9 mcg/ml. This concentration multiplied by the minute volume and the exposure time gives a dose of 1.0 mg; since the rats weighed 0.25 kg, the dose was 4.0 mg/kg. Doses in all trials were calculated as above. This estimates the amount of pentamidine that animals inhaled, not the amount retained.

Experimental Model of PCP

Treatment regimens were tested in the standard animal model of PCP (6). To induce infection with *P. carinii*, rats were immunosuppresed with steriods for twelve weeks while restricted to a low-protein diet and tetracycline. Administration of a test regimen was initiated early during the induction period to determine its effectiveness in preventing PCP and was initiated late during the induction period to determine its effectiveness in treating PCP. Male Sprague-Dawley rats weighing 175-225 g were used. Rats were given twice weekly subcutaneous injections of 75 mg/kg of cortisone acetate, were maintained on an 8% protein diet, and were treated with tetracycline via their drinking water. Rats were sacrificed after twelve weeks of this regimen and the extent of infection was judged by counting cysts in toluidine blue 0-stained smears of lung homogenates. Lung homogenates were prepared by combining a weighed portion of tissue with nine ml of 0.1N HCl per g.

Results

Table 1A shows the levels of pentamidine in different organs of rats that were treated by IM injection with 4.0 mg/kg/day. Animals were sacrificed at 24 h after the last dose. The drug was undetectable (0.8 mcg/g) in the lungs after a single IM dose while the mean level in the kidneys was 26.9 mcg/g. Accumulation of pentamidine after multiple IM doses was highest in the kidneys, liver, and spleen; levels in the kidney were about tenfold higher than in the lung. Tissue concentrations of pentamidine in humans after intravenous infusions of 4.0 mg/kg/day are shown in Table 1B.

Table 2 shows the levels of pentamidine in different organs of rats that were treated with aerosol doses of 0.4 mg/kg/day. Animals were sacrificed at 24 h after the last dose. The drug was undetectable in kidney, spleen, and liver after eight doses of aerosol pentamidine while levels in the lung averaged 60.5 mcg/g.

Figure 2:
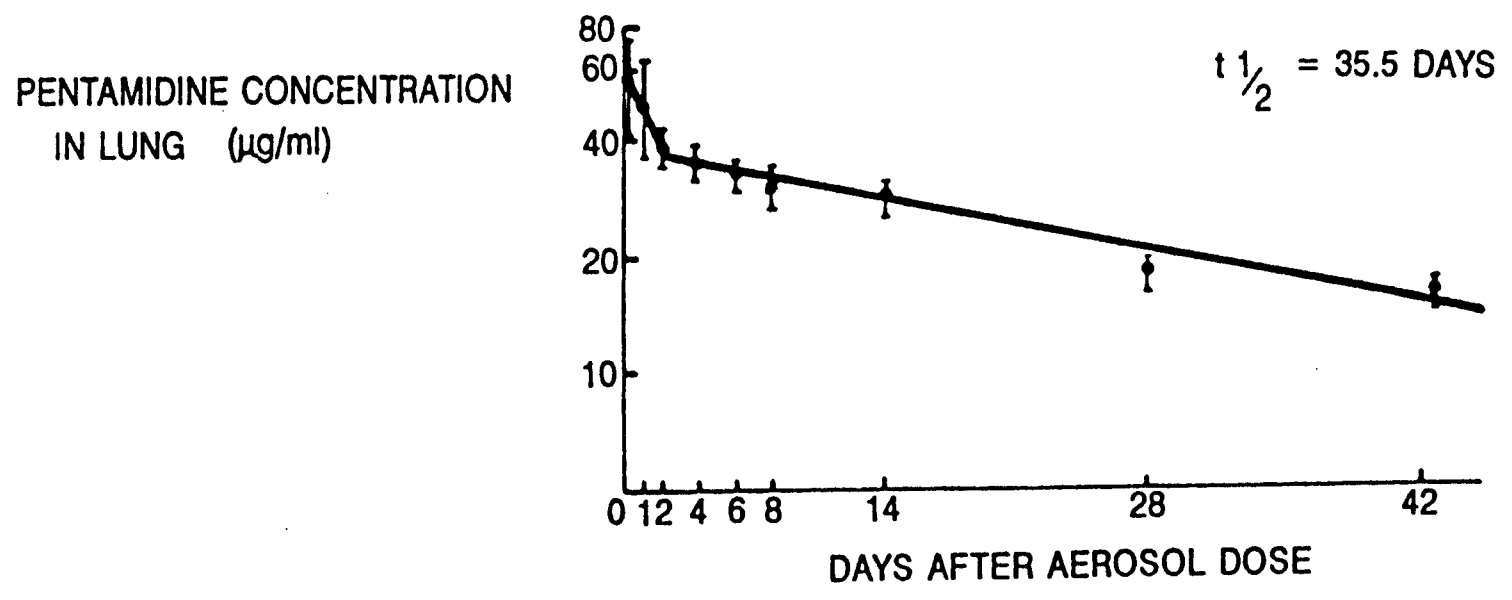

FIG. 2 shows the levels in the lungs of rats that were sacrificed at different times after receiving a single aerosol dose of 4.0 mg/kg. Four rats were studied at each time. There was an early phase of rapid elimination from the lung that may reflect clearance of particles of the drug from large airways. After this period elimination of pentamidine from the lung was extremely slow; the half-life of elimination from days 2-42 was 36 days.

The retention factor for aerosol pentamidine can be estimated from FIG. 2.

TABLE 1A

Tissue Concentrations of Pentamidine in Rats after Intramuscular Injection of 4.0 mg/kg/day

| No. of doses | Pentamidine concentration (mcg/g) | | | | |
|---|---|---|---|---|---|
| | Lung | Kidney | Liver | Spleen | Adrenal |
| 1 | NMA* | 26.9±4.4@ | 4.1±0.4 | 4.5±1.8 | 1.8±1.2 |
| 2 | 3.7±2.6 | 62.4±14.8 | 17.2±7.9 | 27.9±2.9 | 3.3±2.4 |
| 4 | 9.1±6.6 | 83.7±48.8 | 24.6±9.2 | 45.0±17.6 | 5.0±2.4 |

TABLE 1B

Tissue Concentrations of Pentamidine in Humans after Intravenous Infusions of 4.0 mg/kg/day

| No. of doses | Pentamidine concentration (mcg/g) | | | | |
|---|---|---|---|---|---|
| | Lung | Kidney | Liver | Spleen | Adrenal |
| 1 | NMA | 8.5 | 35 | 40 | 19 |
| 2 | NMA | 13 | 23 | 40 | NA# |
| 5 | 42 | 62 | 112 | 28 | NA |
| 15 | 56 | 123 | 300 | 368 | 92 |

*no measurable amount
@mean ± SD (N = 4)
not available

TABLE 2

| No. of doses | Pentamidine concentration (microgram/g) | | |
|---|---|---|---|
| | Lung | Kidney | Spleen |
| 1 | 3.1 ± 1.9 | NMA# | NMA |
| 2 | 12.1 ± 3.0 | NMA | NMA |
| 4 | 17.7 ± 5.5 | NMA | NMA |
| 8 | 60.5 ± 10.2 | NMA | NMA | no measurable amount
mean ± SD (N = 4)

The amount of drug retained in the lungs, by extrapolation of the elimination curve, was about 40 mcg/g; since lung weights averaged 1.5 g, 60 mcg was retained per animal. The amount of drug inhaled by each animal was about 1.0 mg, so about 6.0 percent was retained. Thus, with an aerosol dose of 4.0 mg/kg, the retained dose was 0.24 mg/kg.

Results from trials in the animal model of PCP are shown in Table 3. In Trial I, animals received no treatment or received prophylactic doses of aerosol or IM pentamidine. Animals were treated weekly during weeks 5-11 of the induction period with aerosol pentamidine at 0.4 mg/kg or IM pentamidine at 4.0 mg/kg. All untreated animals had severe PCP at necropsy. Animals that had received prophylactic doses of aerosol pentamidine had lungs that were normal in weight and appearance and cysts of P. carinii were rare or absent in stained smears of lung homogenates. Animals that received prophylactic doses of aerosol pentamidine had more than a thousandfold less severe infection than was seen in control animals. Aerosol pentamidine was more effective in prevention of PCP than tenfold higher doses of IM pentamidine.

In trial II, animals received no treatment or received prophylaxis or treatment with aerosol pentamidine. To test the effectiveness of aerosol pentamidine in prophylaxis of PCP, animals were treated weekly during weeks 7-11 of the induction period with aerosol pentamidine at 0.1 mg/kg. To test the effectiveness of aerosol pentamidine in the treatment of PCP, animals were treated daily for four days during week ten of the induction period with aerosol pentamidine at 0.4 mg/kg. Both the prophylactic and therapeutic regimens were effective.

TABLE 3

| Trial | no. of rats | Pentamidine treatment | | | Lung findings at necropsy | | |
|---|---|---|---|---|---|---|---|
| | | Dose* | Route | Schedule | Weight (g) | Pent (ug/g) | Cysts/hpf # |
| I | 9 | | no treatment | | 3.51 ± 0.86@ | NMA | 824 ± 860 |
| | 8 | 4.0 | IM | weekly, wk 5-11 | 3.28 ± 1.15 | 4.5 ± 1.7 | 102 ± 88 |
| | 8 | 0.4 | aerosol | weekly, wk 5-11 | 1.94 ± 0.21 | 29.7 ± 7.1 | <<1 |
| II | 9 | | no treatment | | 2.57 ± 0.82 | NMA | 247 ± 134 |
| | 9 | 0.2 | aerosol | weekly, wk 7-11 | 1.43 ± 0.31 | 15.2 ± 5.0 | 10.3 ± 8.2 |
| | 8 | 0.4 | aerosol | daily, 4×, wk 10 | 1.20 ± 0.20 | 15.8 ± 10.9 | 20.8 ± 30.8 |
| III | 8 | | no treatment | | 2.29 ± 0.66 | NMA | 504 ± 618 |
| | 8 | 0.8 | aerosol | monthly, wks 4, 8 | 1.26 ± 0.26 | 16.1 ± 3.3 | 4.6 ± 4.2 |
| | 8 | 0.4 | aerosol | biweekly, wks 7, 9, 11 | 1.41 ± 0.64 | 13.4 ± 7.9 | 48 ± 109 |

TABLE 3-continued

| Trial | no. of rats | Pentamidine treatment | | | Lung findings at necropsy | | |
|---|---|---|---|---|---|---|---|
| | | Dose* | Route | Schedule | Weight (g) | Pent (ug/g) | Cysts/hpf # |
| | 7 | 0.4 | aerosol | daily, 4×, wk 12 | 2.08 ± 0.68 | 8.3 ± 6.4 | 188 ± 255 |

*mg/kg of pentamidine isethionate
per high power filed (400×)
@mean ± standard deviation In trial III, both prophylactic regimens were effective and the therapeutic regimen was partially effective.

Within the prophylaxis and treatment groups, the lowest number of cysts were found in animals with the highest concentrations of pentamidine in the lung (data not shown). Retention of aerosol pentamidine was the greater in normal animals and in animals that received early prophylactic doses than it was in animals who were treated when they had severe pneumonia.

Studies of the acute toxicity of aerosol pentamidine were performed in rats. Four rats were treated with four consecutive daily doses of 3.2 mg/kg of aerosol pentamidine and were sacrificed at 24 h after the last dose (total dose; 12.8 mg/kg). The mean concentration of pentamidine was 291 mcg/g in the lungs and 7.2 mcg/g in the kidneys. Treatments were well-tolerated. Lungs were normal in weight and appearance. Stained sections of the lungs were examined and no histopathologic changes were found. There were rare foci of mild thickening of interalveolar septae containing a few histiocytes and some congestion. Rare lymphoid aggregates were seen in peribronchial regions. These were also seen in sections from control animals and are common findings in normal rat lung. The presence of high concentrations of pentamidine in the lungs appears to provoke little or no toxicity.

II. Clinical Studies

Patient Eligibility

Patients were 18 years old or older and outpatients judged free of any imminently-critical medical problems. All patents received a complete physical examination and medical history evaluation. Pretreatment laboratory studies included a CBC with differential and platelet count, a biochemical screening profile, chest X-ray, and pulmonary function tests including spirometry and measurement of diffusion capacity.

Patients were not receiving any other investigational agents for chemoprophylaxis of PCP, e.g. sulfamethoxazole-trimethoprim (bactrim), sulfadoxine-pyrimethamine (fansidar), dapsone, or IV pentamidine. They could have been receiving investigational agents for treatment of AIDS such as azidothymidine (AZT) or for treatment of KS or opportunistic infections other than PCP.

All patients had:
1) AIDS or ARC as defined by the Centers for Disease Control;
2) a normal chest X-ray or minimal . abnormalities that have diminished or stabilized over the previous month;
3) WBC 1,000/mm3 and platelets less than or equal to 60,000/mm3;
4) adequate pulmonary function (vital capacity 80% of predicted; forced expiratory volume, 1 sec less than or equal to 65% of total FEV; and corrected pulmonary diffusion capacity less than or equal to 60% of predicted).

Patients who had inadequate pulmonary function according to the above criteria were only enrolled after evaluation by the Infectious Diseases and Pulmonary Services. These patients were enrolled if PCP could be ruled out (e.g., by rest and exercise blood gases, gallium scan, or bronchoscopy) and if pulmonary function is only marginally inadequate and is considered likely to remain stable or improve. This category was included because we expeced, based on past experience, that pretreatment evaluation could reveal previously unsuspected pulmonary disease in a small number of patients.

Aerosol Apparatus

A hand-held ultrasonic nebulizer (Siemens Micro-Inhalator S, model no. TV 7000) was used to administer aerosol pentamidine. Each patient was issued a device at the start of the study. These devices were labeled with the patient's code number. The devices are simple to operate and their sterility was ensured as components were replaced after a single use. New sterile plastic reservoirs for the drug solution and new sterile suction rods were used for each treatment.

Administration of the Drag

Each aerosol treatment was given over 15-30 minutes. The nebulizer was loaded with 3.0 ml of solution of pentamidine isethionate in sterile water. Ampules containing pentamidine (Pentam 300, LyphoMed, Melrose Park, Ill.) were obtained from the pharmacy by prescription. The sterile ampules contained 300 mg of lyophilized pentamidine isethionate and were intended as a single dose vial for IM and IV use. Using aseptic techniques, 10.0 ml of sterile pyrogen-free water were added to an ampule to yield a solution containing 30.0 mg/ml of pentamidine isethionate. 1.0, 1.5,or 2.0 ml aliquots were added to the nebulizer reservoir for doses of 30, 45, or 60 mg, respectively. Sterile pyrogen-free water was added to yield a total volume of 3.0 ml. Treatments were administered by a physician or registered nurse.

Pharmacokinetic Studies

Pentamidine concentrations were measured in serum and urine samples collected during the treatment period. A urine sample was obtained from each patient before treatment numbers 1, 6, 10, 16, and 28. A serum sample was obtained from each patient before the first treatment and at 0–15 min after treatment numbers 1, 6, 10, 16, and 28.

Evaluation of Toxicity

General Procedure

The aim was to determine if aerosol pentamidine cause systemic or pulmonary toxicity. The most common adverse reactions to pentamidine, when it is given IM or IV, are hypotention, hypoglycemia, and renal failure (4). It was not expected that these would be observed with aerosol pentamidine because this route of administration limits delivery of the drug to the lungs and there is little or no systemic absorption of the drug after oral administration. None of these reactions have been seen in patients treated with a biweekly dose of 30 mg. Signs of systemic toxicity were monitored. To detect adverse effects on the lungs, pulmonary function was monitored.

During the study all medical problems revealed by questioning or examining the patient were recorded. All problems were judged a concomitant illness or adverse reaction based on the following definitions. A concomitant illness was an experience not related to use of the study drug and included any event attributable to enviromnmental, systemic, accidental factors, or concomitant medication. An adverse reaction was an unwanted experience which might be related to use of the study drug and includes any side effect, toxicity, or sensitivity reaction to the study drug. All adverse reactions were rated as mild, moderate, or severe.

Patients were interviewed before and after each treatment and any adverse reactions, complaints, or comments recorded. This data and results of physical and laboratory examinations were reviewed weekly and summary reports prepared quarterly.

The following studies were performed on all participants before the first treatment and at treatment numbers 6, 10, 16, and 28.

1) medical examination: included complete or interim medical history and physical examination;

2) laboratory tests: included biochemical screening profile and complete blood count with differnetial;

3) pulmonary function tests: included spirometry and measurement of diffusion capacity.

Patients who in the preliminary evaluation were found to have reduced pulmonary function (D1 CO less than 60% of predicted) also underwent all of the examinations listed above at treatments no. 4 and 20. A chest x-ray was obtained at entry and at treatments no. 16 and 28.

Evaluation of Effectiveness

Prophylaxis was judged effective for an individual patient if that patient had no proven or probable episodes of PCP. Prophylaxis was considered a proven failure if a patinet developed pneumonia and *P. carinii* was found in stained preparations obtained by bronchoscopy or lung biopsy. Prophylaxis was considered a probable failure if a patient develops pneumonia and responded to empiric treatment with SXT the case was considered inevaluable because a bacterial etiology for the pneumonia could not be ruled out. If a patient died and no autopsy was perfomed, the case was considered not evaluable unless there was evidence that the patient had good antemortem pulmonary function and died from other causes. If the latter conditions were met, the case was considered a probable success.

Criteria for Discontinuing

A dose level was discontinued if a severe adverse reaction was observed in any patient or if moderate adverse reactions were observed in more than three patients. Administration of the drug to individual patients was discontinued if repeated mild adverse reactions were experienced.

Treatment was discontinued if any patient had interim results from biochemical or hematologic tests that exceeded the limits used to established patient eligibility unless the abnormality was judged unrelated to use of aerosol pentamidine.

Treatment was discontinued if a patient had, compared to baseline studies, a 20% decline in vital capacity or in corrected diffusion capacity or forced expiratory volume (1 sec).

Any patient who developed a severe opportunistic infection or other concomitant illness necessitating hospitalization was discontinued from the study. Unless the infection is PCP, treatment with aerosol pentamidine was resumed when the patient was discharged from the hospital.

Any patient could elect to discontinue participation at anytime.

Summary

Trials of the safety and effectiveness of aerosol pentamidine in patients with AIDS or ARC have been underway for one year. Initially twelve patients were treated with biweekly doses of 30 mg of aerosol pentamidine. The treatment period was three months; patients were examined before and after each treatment and underwent pulmonary function testing and biochemical and hematologic tests before treatment no. 1 and after treatment nos. 1, 2, 4, and 6. No adverse reactions were seen, all patients had stable or improving pulmonary function, and no patient had a proven or possible episode of PCP.

In the next phase a total of 60 patients were enrolled; all patients received biweekly doses of 30 mg of aerosol pentamidine. A total of 650 treatments were given. Treatment periods ranged from 1–12 months. No proven adverse reactions have been observed. A single patient developed a severe skin rash after his fifth dose. He had no reactions after his first four doses and was receiving several other medications at the time the rash developed. His rash has since disappeared and the patient is currently receiving aerosol pentamidine elsewhere and is tolerating it well. Five proven episodes of PCP have occurred among patients who received biweekly doses of 30 mg; six proven episodes of PCP have occurred among patients who were treated with this dose, but who skipped one or more scheduled doses.

In the next phase patients were randomized to receive doses of 30, 45, or 60 mg of aerosol pentamidine. Treatments are administered weekly for the first four weeks and then biweekly—this new schedule was designed to more rapidly establish protective levels of pentamidine. A total of 73 patients were enrolled over the past two months with approximately equal numbers at each dose level. Because of evidence that the 30 mg dose was not reliably protective and because the 45 mg and 60 mg doses appear to be well tolerated, we have recently discontinued the 30 mg dose. Patients who were receiving the low dose have since been randomized to receive either 45 or 60 mg. To date two patients receiving 45 mg have had proven episodes of PCP. Both were very mild episodes.

In conclusion, a total of 960 doses of aerosol pentamidine have been administered to a total of 116 patients. The longest period of followup has been one year. No participant has had a significant decline in pulmonary function, abnormalities in biochemical or hematologic tests, or chest x-ray changes attributable to aerosol pentamidine. The treatments appear to be well tolerated and there is preliminary evidence that they are at least partially protective. A total of seven mild cases of PCP has been seen. If aerosol pentamidine had been ineffective, 30–45 cases would have been seen.

References

1. Centers for Disease Control, Morbid Mortal Weekly Rep. 1981; 30:250

2. Centers for Disease Control, AIDS Weekly Surv. Rep. 1985; Dec. 30

3. Gordin, F. M., Simon, G. L., Wofsy, C. B., Mills, J., Adverse Reactions to Trimethoprim-sulfamethoxazole in Patients with the Acquired Immune Deficiency Syndrome. Ann Int. Med. 1984; 100:495-9

4. Navin, T. R., Fontaine, R. E., Intravenous Versus Intramuscular Administration of Pentamidine [leeter]. N Engl. J. Med. 1984; 311:1701-2

5. Bernard, E. M., Donnelly, H. J., Maher, M. P., Armstrong, D. Use of a New Disassay to Study Pentamidine Pharmacokinetics. J. Infect. Dis. 1985; 152:750-4

6. Frenkel, J. K., Good, J. T., Schultz, J. A., Latent Pneumocystis Infection of Rats, Relapse, and Chemotherapy, Lab Invest. 1966; 15:1559-77

7. Demarchi J. Rapport, Sur la Chiminoprophylaxie de la Trypanosomiase a *T. gambiense.* in Comite Scientifique International de Recherches sur les Trypanosomiases. Publication 41. Brussells: Commission de Cooperation technique en Afrique au Sud du Sahara, 1958

8. Van Hoof, L., Henrard, C., Peel, E., Pentamidine in the Prevention and Treatment of Trypanosomiasis. Trans. Roy. Soc. Trop. Med. Hyg. 1944; 37: 271

9. Western, K. A., Norman L., Kaufmann A. F., Failure of Pentamidine Isethionate To Provide Chemoprophylaxis Against *Pneumocystis carinii* Infectionin In Rats., J. Infect. Dis. 197514 131: 273-6

10. Waldman, R. H., Pearce, D. E., Martin, R. A. Pentamidine Isethionate in Lungs, Livers, and Kidneys of Rats After Aerosol or Intramuscular Administration. Amer. Rev. Resp. Dis. 1973; 108: 1004-6

11. Bernard, E. M., Donnelly, H. J., Tsang, S., Huang, A., Armstong, D., Aerosol Pentamidine is Effective in the Prevention and Treatment of *Pneumocystis Carinii* Pneumonia (PCP) in the Rat Model. Annual meeting of the American Society for Microbology. Abstract number A81

What is claimed is:

1. A method of reducing the occurrence of *Pneumocystis carinii*-caused pneumonia in a human subject infected with the virus which causes acquired immune deficiency syndrome (AIDS) and susceptible to infection by *Pneumocystis carinii* comprising administering to the subject above 30 mg up to about 500 mg of pentamidine isethionate in aerosol form so as to prevent infection by *Pneumocystis carinii* and thus reduce the occurrence of *Pneumocystis carinii*-caused pneumonia.

2. The method of claim 1, wherein the pentamidine isethionate in aerosol form is administered with an ultrasonic nebulizer.

3. The method of claim 1, wherein the amount of pentamidine isethionate in aerosol form effective to prevent infection by *Pneumocystis carinii* is between about 0.1 microgram/ml and about 200 microgram/ml.

4. The method of claim 1, wherein above 30 mg up to about 60 mg of pentamidine isethionate is administered to the subject.

* * * * *